United States Patent
Matsuura et al.

(10) Patent No.: US 11,725,161 B2
(45) Date of Patent: Aug. 15, 2023

(54) CARBOXYLIC ACID ESTER COMPOUND, PRODUCTION METHOD THEREOF, AND FRAGRANCE COMPOSITION

(71) Applicant: MITSUBISHI GAS CHEMICAL COMPANY, INC., Chiyoda-ku (JP)

(72) Inventors: Yutaka Matsuura, Niigata (JP); Tatsuya Utamura, Okayama (JP); Tomohiko Hakamata, Kanagawa (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 267 days.

(21) Appl. No.: 17/291,022

(22) PCT Filed: Nov. 7, 2019

(86) PCT No.: PCT/JP2019/043662
§ 371 (c)(1),
(2) Date: May 4, 2021

(87) PCT Pub. No.: WO2020/100708
PCT Pub. Date: May 22, 2020

(65) Prior Publication Data
US 2022/0041955 A1    Feb. 10, 2022

(30) Foreign Application Priority Data

Nov. 16, 2018 (JP) .................. 2018-216004

(51) Int. Cl.
| | |
|---|---|
| *C11B 9/00* | (2006.01) |
| *C07C 69/753* | (2006.01) |
| *C07C 67/38* | (2006.01) |
| *C07C 67/36* | (2006.01) |
| *C07C 67/08* | (2006.01) |
| *C07C 51/58* | (2006.01) |

(52) U.S. Cl.
CPC ............ *C11B 9/0046* (2013.01); *C07C 51/58* (2013.01); *C07C 67/08* (2013.01); *C07C 67/36* (2013.01); *C07C 67/38* (2013.01); *C07C 69/753* (2013.01)

(58) Field of Classification Search
CPC ....... C11B 9/0046; C07C 67/38; C07C 67/08; C07C 67/36; C07C 69/753; C07C 51/58
See application file for complete search history.

(56) References Cited

U.S. PATENT DOCUMENTS

| | | | |
|---|---|---|---|
| 4,310,681 A | 1/1982 | Klemarczyk et al. | |
| 4,312,888 A | 1/1982 | Klemarczyk et al. | |
| 4,319,036 A | 3/1982 | Klemarczyk et al. | |
| 4,347,858 A | 9/1982 | Klemarczyk et al. | |
| 4,350,823 A | 9/1982 | Klemarczyk et al. | |
| 4,357,246 A | 11/1982 | Klemarczyk et al. | |
| 4,357,253 A | 11/1982 | Klemarczyk et al. | |
| 4,367,158 A * | 1/1983 | Sprecker ................. | C11D 3/50 512/19 |
| 4,374,054 A | 2/1983 | Klemarczyk et al. | |
| 4,386,064 A | 5/1983 | Klemarczyk et al. | |
| 4,395,366 A | 7/1983 | Klemarczyk et al. | |
| 4,431,577 A | 2/1984 | Klemarczyk et al. | |
| 2013/0184486 A1 * | 7/2013 | Kitamura ................ | C07C 67/14 560/114 |
| 2019/0241833 A1 | 8/2019 | Kitamura | |

FOREIGN PATENT DOCUMENTS

| | | |
|---|---|---|
| CN | 103415500 A | 11/2013 |
| JP | 57-8757 A | 1/1982 |
| JP | 60-190738 A | 9/1985 |
| WO | WO 2012/063433 A1 | 5/2012 |
| WO | WO 2018/051776 A1 | 3/2018 |

OTHER PUBLICATIONS

International Search Report dated Dec. 24, 2019 in PCT/JP2019/043662 filed Nov. 7, 2019, 2 pages.

* cited by examiner

*Primary Examiner* — Yate' K Cutliff
(74) *Attorney, Agent, or Firm* — Oblon, McClelland, Maier & Neustadt, L.L.P.

(57) ABSTRACT

The present invention has an object of providing a carboxylate compound that is useful as a raw material for fragrance compositions and has a fruity aroma, a method for producing the same, and a fragrance composition containing the carboxylate compound.
The carboxylate compound of the present invention is represented by Formula (1).

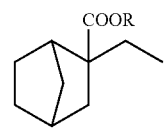

(1)

where, R is an alkyl group having from 2 to 6 carbons.

4 Claims, No Drawings

CARBOXYLIC ACID ESTER COMPOUND, PRODUCTION METHOD THEREOF, AND FRAGRANCE COMPOSITION

TECHNICAL FIELD

The present invention relates to a novel carboxylate compound, a production method thereof, and a fragrance composition containing the carboxylate compound, and in particular, the present invention relates to a carboxylate compound that is useful as a raw material for fragrance compositions, a production method thereof, and a fragrance composition containing the carboxylate compound.

BACKGROUND ART

Some esters are known to be compounds that are useful as fragrances. For example, geranyl acetate having a rose-like aroma, methyl jasmonate having a jasmine-like sweet aroma, Fruitate (ethyl tri cyclo[5.2.1.0$^{2,6}$]decane-2-carboxylate) having a fruity scent, and methyl benzoate with an intense dry fruity scent are useful as ingredients for fragrance compositions. Furthermore, Patent Document 1 describes that a carboxylate compound that is a derivative of camphene has a refreshing pine-like aroma.

CITATION LIST

Patent Documents

Patent Document 1: WO 2012/063433

SUMMARY OF INVENTION

Technical Problem

A problem to be addressed by the present invention is to provide a novel carboxylate compound having a fruity aroma, a method for producing the same, and a fragrance composition containing the carboxylate compound.

Solution to Problem

The present inventors synthesized various compounds and studied the aromas thereof, and they discovered that certain carboxylate compounds have a fruity aroma, thereby arriving at the present invention.

The present invention provides the following aspects <1> to <4>.

<1> A carboxylate compound represented by Formula (1).

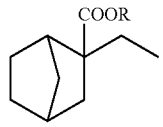
(1)

where, R is an alkyl group having from 2 to 6 carbons.

<2> The carboxylate compound according to <1>, wherein R is an ethyl group, a n-propyl group, or an isopropyl group.

<3> A fragrance composition containing a carboxylate compound represented by Formula (1).

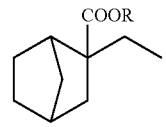
(1)

where, R is an alkyl group having from 2 to 6 carbons.

<4> A method for producing a carboxylate compound represented by Formula (1) by reacting a compound represented by Formula (2) with carbon monoxide in the presence of hydrogen fluoride, and then reacting with an alcohol having from 2 to 6 carbons.

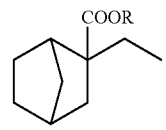
(1)

where, R is an alkyl group having from 2 to 6 carbons.

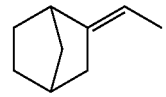
(2)

Advantageous Effects of Invention

The carboxylate compound of the present invention has a fruity aroma and is useful as a perfuming component in a wide range of products such as toiletry articles, soaps, and clothing detergents. Furthermore, according to the method for producing a carboxylate compound of the present invention, the carboxylate compound can be produced in an industrially advantageous manner.

DESCRIPTION OF EMBODIMENTS

The present invention will be described below using embodiments. Note that in the following description, descriptions of "from A to B" indicating a numerical range indicate "greater than or equal to A and less than or equal to B" (when A<B), or "less than or equal to A and greater than or equal to B" (when A>B). In other words, descriptions of "from A to B" indicate numerical ranges including the endpoints A and B.

Furthermore, the terms parts by mass and mass % are synonymous with the terms parts by weight and wt. %, respectively.

[Carboxylate Compound]

A carboxylate compound of the present invention is represented by Formula (1) below.

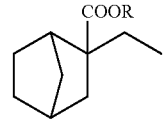
(1)

where, R is an alkyl group having from 2 to 6 carbons.

In Formula (1), R is an alkyl group having from 2 to 6 carbons. The alkyl group having from 2 to 6 carbons is preferably a linear or branched alkyl group, and examples thereof include an ethyl group, a n-propyl group, an isopropyl group, a n-butyl group, an isobutyl group, a tert-butyl group, a pentyl group, and a hexyl group. Among these, from the perspective of the aroma property, an ethyl group, a n-propyl group, and an isopropyl group are preferable, and an ethyl group is more preferable.

The carboxylate compound represented by Formula (1) has a stereoisomer, and may be an exo-isomer or an endo-isomer, or a mixture of exo- and endo-isomers at any ratio, and it is not particularly limited.

Of these, an exo-isomer is preferable from the perspective of production ease and the aroma property.

[Method for Producing a Carboxylate Compound]

The carboxylate compound of the present invention (the carboxylate compound represented by Formula (1)) can be advantageously produced industrially by a method in which a compound represented by Formula (2) is reacted with carbon monoxide in the presence of hydrogen fluoride (hereinafter, also referred to as "HF"), followed by a reaction with an alcohol having from 2 to 6 carbons.

Specifically, a compound represented by Formula (2) is subjected to carbonylation by reacting with carbon monoxide in the presence of hydrogen fluoride (HF), whereby an acid fluoride represented by Formula (3) is obtained. Next, the acid fluoride represented by Formula (3) is esterified by reacting it with an alcohol having from 2 to 6 carbons in the presence of hydrogen fluoride.

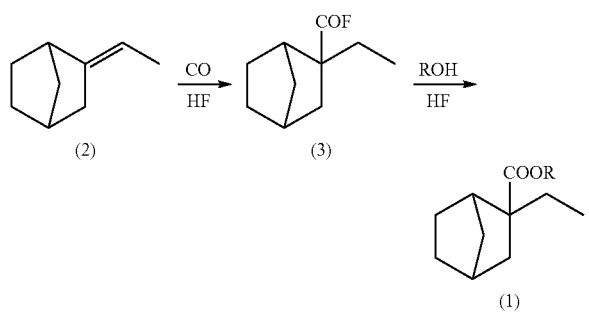

where, R is an alkyl group having from 2 to 6 carbons.

(Compound Represented by Formula (2))

The compound represented by Formula (2) is 2-ethylidene norbornane, and can be obtained by hydrogenation of 5-ethylidene-2-norbornene (ENB). Note that ENB is known as a raw material for ethylene-propylene-diene (EPDM) rubber.

(Carbon Monoxide)

The carbon monoxide used in the present invention may contain an inert gas such as nitrogen or methane. The partial pressure of the carbon monoxide during the reaction is in a range of preferably from 0.5 to 5 MPaG, and more preferably from 1 to 3 MPaG. If the partial pressure of carbon monoxide is higher than 0.5 MPaG, the carbonylation reaction proceeds sufficiently, and heterogeneity and side reactions such as polymerization do not occur simultaneously, and an alicyclic carbonyl compound that is the target product can be produced at a high yield. Furthermore, from the perspective of equipment load, the carbon monoxide partial pressure is preferably not greater than 5 MPaG.

(Hydrogen Fluoride)

The HF used in the present invention is a solvent for the reaction, and is also a catalyst and a raw material, and therefore use of a substantially anhydrous HF is preferable. The usage amount of HF in terms of a molar ratio with respect to the raw material compound represented by Formula (2) is preferably from 4 to 25 times, and more preferably from 6 to 15 times. If the molar ratio of HF is 4 times or greater, the carbonylation reaction proceeds efficiently, heterogeneity and side reactions such as polymerization can be suppressed, and a carbonyl compound that is the target product can be produced at a high yield. Furthermore, from the perspective of raw material costs and productivity, use of HF at a molar ratio of 25 times or less is preferable.

(Reaction Solvent)

In the carbonylation reaction, a solvent that thoroughly dissolves the raw materials and is inert to HF may be used. For example, saturated hydrocarbon compounds such as hexane, heptane, and decane can be used. The presence or absence and usage amount of the solvent are not particularly limited and may be selected as appropriate. However, from the perspective of suppressing a polymerization reaction and improving the yield, the mass ratio of the solvent with respect to the raw material compound of Formula (2) is preferably from 0.2 to 2.0 times, and from the perspectives of productivity and energy efficiency, the mass ratio of the solvent is preferably from 0.5 to 1.2 times.

(Reaction Conditions of the Carbonylation Reaction)

The carbonylation reaction may be performed in any manner, for example, in a batch, in a semi-continuous, or in a continuous manner, which is not particularly limited.

The reaction temperature of the carbonylation reaction is in a range of preferably from −50° C. to 30° C., and more preferably from −30° C. to 20° C. From the perspective of the reaction rate, the reaction is preferably carried out at a temperature of −50° C. or higher. Furthermore, from the perspective of suppressing the production amount of isomers, the reaction is preferably carried out at a temperature of 30° C. or lower.

The reaction time of the carbonylation reaction is preferably not less than 1 hour from the perspective of causing complete reaction, and is preferably not longer than 5 hours from the perspective of the reaction efficiency. The reaction endpoint is not particularly limited, and for example, the reaction may be stopped when the absorption of carbon monoxide stops.

In the carbonylation reaction, an acid fluoride (Formula (3)) is produced by HF and carbon monoxide. The resulting acid fluoride reaction solution (carbonylation reaction solution) may be purified by a typical method such as distillation after excess HF has been distilled off, and the purified acid fluoride solution may then be used as a raw material in a subsequent esterification step. However, ordinarily, a method of producing a carboxylate compound by reacting, as is, the carbonylation reaction solution containing an HF catalyst with an alcohol is adopted.

(Alcohol)

The alcohol used in the present invention is an alcohol having from 2 to 6 carbons.

The alcohol having from 2 to 6 carbons is not particularly limited, and can be appropriately selected according to the purpose, and examples include ethanol, n-propanol, isopropanol, n-butanol, isobutanol, tert-butanol, pentanol, and hexanol. Among these, ethanol, n-propanol, isopropanol, n-butanol, and isobutanol are preferable, ethanol, n-propanol, and isopropanol are more preferable, and ethanol is even more preferable.

The usage amount of the alcohol having from 2 to 6 carbons is not particularly limited, and can be appropriately selected according to the purpose, and with respect to the raw material compound of Formula (2), the molar ratio of the usage amount thereof is preferably from 0.5 to 2.0 times, more preferably from 0.8 to 1.7 times, and even more preferably from 1.0 to 1.7 times.

(Reaction Conditions for the Esterification Reaction)

From the perspective of improving yield, the reaction temperature of the esterification reaction is preferably not lower than −20° C., and from the perspective of suppressing side reactions such as ester decomposition and dehydration of the added alcohol, the reaction temperature is preferably not higher than 20° C.

The reaction time of the esterification reaction is preferably not less than 0.5 hours from the perspective of causing complete reaction, and is preferably not longer than 3 hours from the perspective of reaction efficiency. The reaction endpoint is not particularly limited, and for example, the reaction may be stopped when no increase in reaction heat is observed.

The esterified product thus obtained is a solution of carboxylate/HF complex. By heating the solution of carboxylate/HF complex, the bonds between the carboxylate and HF are decomposed, and HF can be vaporized, recovered, and reused. The decomposition operation of this complex must be conducted as quickly as possible to avoid deterioration by heating, isomerization and the like of the product. In order to rapidly advance the thermal decomposition of the complex, it is preferable, for example, to decompose the complex under reflux of a solvent inert to HF (for example, a saturated aliphatic hydrocarbon such as heptane or an aromatic hydrocarbon such as toluene). In addition, when the reaction solution is extracted in ice water, preferably, for example, the reaction solution is extracted into ice water from the bottom of an autoclave and separated into an oil phase and an aqueous phase, after which the oil phase is washed twice with a 2 mass % sodium hydroxide aqueous solution and twice with distilled water, and then dehydrated with anhydrous sodium sulfate. The thus obtained solution is then passed through an evaporator to remove low-boiling-point substances and the like, and then subjected to rectification with a rectifier having a theoretical plate number of approximately 20, and thereby a purified carboxylate compound can be obtained.

Note that the carboxylate compound of the present invention can be produced by a method other than that described above. For example, as indicated in the schemes below, an aldehyde compound (Formula (4)) obtained by a Diels-Alder reaction between cyclopentadiene and 2-ethylacrolein can be oxidized to obtain a carboxylic acid compound (Formula (5)), the carboxylic acid compound is then reacted with an alcohol having from 2 to 6 carbons to obtain an ester compound (Formula (6)), and the ester compound can then be hydrogenated to obtain the carboxylate compound of the present invention (carboxylate compound represented by Formula (1)). Furthermore, the carboxylic acid compound represented by Formula (5) can be obtained by a Diels-Alder reaction between cyclopentadiene and 2-ethyl acrylic acid (2-methylene butyric acid).

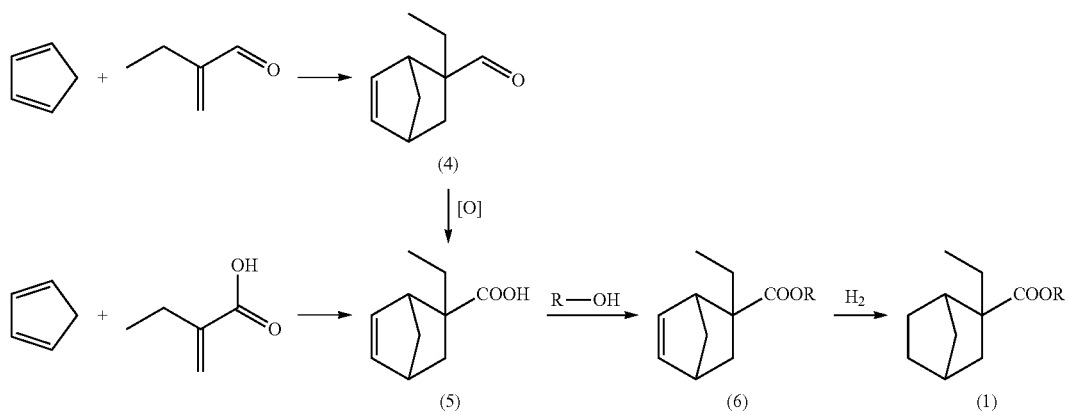

where, R is an alkyl group having from 2 to 6 carbons.

The carboxylate compound of the present invention has a fruity aroma, and therefore can be used, alone or in combination with other components, as a perfuming component in products such as soaps, shampoos, rinses, detergents, cosmetics, spray products, aromatic substance, perfumery, and bath salts. Use as a synthetic intermediate for food products, pharmaceuticals, agrochemicals, liquid crystals, and the like can also be anticipated.

[Fragrance Composition]

The fragrance composition of the present invention contains a carboxylate compound represented by Formula (1).

The fragrance composition of the present invention can be obtained by mixing and blending one or more types of carboxylate compounds represented by Formula (1) into another fragrance component normally used or a desired fragrance composition. The blending amount of the carboxylate compound represented by Formula (1) differs depending on the type of fragrance composition, the type of targeted aroma, the intensity of the aroma, and the like, but adding from 0.01 to 90 mass % to the fragrance composition is preferable, and adding from 0.1 to 50 mass % is more preferable.

The other fragrance component that can be used in combination with the carboxylate compound of the present invention is not particularly limited, and can be appropriately selected according to the purpose. Examples include:

hydrocarbons such as limonene, α-pinene, β-pinene, terpinene, cedrene, longifolene, and valencene;

alcohols such as linalool, citronellol, geraniol, nerol, terpineol, dihydromyrcenol, ethyllinalool, farnesol, nerolidol, cis-3-hexenol, cedrol, menthol, borneol, β-phenylethyl alcohol, benzyl alcohol, phenyl hexanol, 2,2,6-trimethylcyclohexyl-3-hexanol, 1-(2-t-butylcyclohexyloxy)-2-butanol, 4-isopropylcyclohexane methanol, 4-methyl-2-(2-methylpropyl)tetrahydro-2H-pyran-4-ol, 2-methyl-4-(2,2,3-trimethyl-3-cyclopenten-1-yl)-2-buten-1-ol, 2-ethyl-4-(2,2,3-trimethyl-3-cyclopenten-1-yl)-2-buten-1-ol, isocamphylcyclohexanol, and 3,7-dimethyl-7-methoxyoctan-2-ol;

phenols such as eugenol, thymol, and vanillin;

esters such as linalyl formate, citronellyl formate, geranyl formate, n-hexyl acetate, cis-3-hexenyl acetate, linalyl acetate, citronellyl acetate, geranyl acetate, nellyl acetate, terpinyl acetate, nopil acetate, bornyl acetate, isobornyl acetate, o-t-butylcyclohexyl acetate, p-t-butylcyclohexyl acetate, tricyclodecenyl acetate, benzyl acetate, styralyl acetate, cinnamyl acetate, dimethylbenzyl carbinyl acetate, 3-pentyltetrahydropyran-4-yl acetate, citronellyl propionate, tricyclodecenyl propionate, allylcyclohexyl propionate, ethyl-2-cyclohexyl propionate, benzyl propionate, citronellyl butyrate, dimethylbenzylcarbinyl n-butyrate, tricyclodecenyl isobutyrate, methyl-2-nonenoate, methyl benzoate, benzyl benzoate, methyl cinnamate, methyl salicylate, n-hexyl salicylate, cis-3-hexenyl salicylate, geranyl tiglate, cis-3-hexenyl tiglate, methyl jasmonate, methyldihydro jasmonate, methyl-2,4-dihydroxy-3,6-dimethyl benzoate, ethylmethylphenyl glycidate, methyl anthranilate, and fruitate;

aldehydes such as n-octanal, n-decanal, n-dodecanal, 2-methylundecanal, 10-undecenal, citronellal, citral, hydroxycitronellal, dimethyl tetrahydrobenzaldehyde, 4(3)-(4-hydroxy-4-methylpentyl)-3-cyclohexene-1-carboaldehyde, 2-cyclohexyl propanal, p-t-butyl-α-methylhydrocinnamic aldehyde, p-isopropyl-α-methylhydrocinnamic aldehyde, p-ethyl-α,α-dimethylhydrocinnamic aldehyde, α-amylcinnamic aldehyde, α-hexylcinnamic aldehyde, piperonal, and α-methyl-3,4-methylenedioxyhydrocinnamic aldehyde;

ketones such as methylheptenone, 4-methylene-3,5,6,6-tetramethyl-2-heptanone, amylcyclopentanone, 3-methyl-2-(cis-2-penten-1-yl)-2-cyclopenten-1-one, methylcyclopentenolone, rose ketone, γ-methylionone, α-ionone, carbone, menthone, camphor, nootkatone, benzylacetone, anysilacetone, methyl-β-naphthylketone, 2,5-dimethyl-4-hydroxy-3(2H)-furanone, maltol, 7-acetyl-1,2,3,4,5,6,7,8-octahydro-1,1,6,7-tetramethyl naphthalene, muscone, civetone, cyclopentadecanone, and cyclohexedecenone;

acetals and ketals such as acetoaldehyde ethylphenylpropyl acetal, citraldiethyl acetal, phenylacetoaldehyde glycerin acetal, and ethylacetoacetate ethylene glycol ketal;

ethers such as anetol, β-naphthylmethyl ether, β-naphthylethyl ether, limonene oxide, rose oxide, 1,8-cineol, racemic or optically active dodecahydro-3a,6,6,9a-tetramethylnaphtho[2,1-b]furane;

nitriles such as citronellyl nitrile;

lactones such as γ-nonalactone, γ-undecalactone, σ-decalactone, γ-jasmolactone, cumarin, cyclopentadecanolide, cyclohexadecanolide, ambrettolide, ethylene brassylate, and 11-oxahexadecanolide; and natural essential oils and natural extracts of orange, lemon, bergamot, mandarin, peppermint, spearmint, lavender, chamomile, rosemary, eucalyptus, sage, basil, rose, geranium, jasmine, ylang-ylang, anise, clove, ginger, nutmeg, cardamom, cedar, Japanese cypress, vetiver, patchouli, and labdanum, Moreover, these other fragrance components may be blended alone or in a combination of two or more.

The carboxylate compound represented by Formula (1) imparts an excellent fruity aroma, and therefore the fragrance composition containing the carboxylate compound represented by Formula (1) can be used as an aroma component for various products such as perfumery and cosmetics, health and hygiene materials, miscellaneous goods, food products, quasi-drugs, and pharmaceuticals in order to improve the aroma of the product to be blended.

The fragrance composition containing the carboxylate compound represented by Formula (1) can be used as a fragrance component for various products including, for example, fragrance products, such as perfumes and colognes; cosmetics for hair, such as shampoos, rinses, hair tonics, hair creams, mousses, gels, pomades, sprays; cosmetics for skin, such as face lotions, serums, creams, emulsions, facial masks, foundations, face powders, lipsticks, and various makeups; various detergents for health and sanitation, such as dish detergents, laundry detergents, softeners, disinfectant detergents, odor eliminating detergents, indoor fragrances, furniture care agents, glass cleaners, furniture cleaners, floor cleaners, disinfectants, insecticides, and bleaching agents; quasi-drugs, such as toothpaste, mouthwash, bath salts, antiperspirants, and perm solutions; miscellaneous goods such as toilet paper and tissue paper; pharmaceuticals; and food products.

Furthermore, the amount of the fragrance composition of the present invention that is blended into a product is not particularly limited, and can be appropriately selected according to the purpose, but the amount of the carboxylate compound represented by Formula (1) that is blended into the product is preferably from 0.001 to 50 mass %, and more preferably from 0.01 to 20 mass %.

EXAMPLES

The present invention will be described more specifically hereinafter using examples and comparative examples, but the present invention is not limited to these examples.

<Gas Chromatography Analysis Conditions>

Gas chromatography was implemented using a gas chromatograph ("GC-2010Plus", available from Shimadzu Corporation) and a capillary column ("HR-1" (0.32 mmφ×25 m, available from Shinwa Chemical Industries Ltd.). As the condition for temperature increase, the temperature was increased from 100° C. to 310° C. at a rate of 5° C./minute.

<GC-MS>

A GC-MS spectrometer JMS-T100GCV available from JEOL Ltd. was used.

<$^1$H-NMR and $^{13}$C-NMR Spectroscopy>

Measurements were implemented under the following conditions.

Device: NMR spectrometer JNM-ECA500, available from JEOL Ltd.

Internal standard substance: tetramethylsilane (TMS)

<Carboxylate Compound Yield, Isomer Ratio>

Carboxylate compound yield (mol %)=(number of moles of carboxylate compound)/(number of moles of 2-ethylidene norbornane)×100

Isomer ratio (%)=(number of moles of 2-ethylnorbornane-exo-2-carboxylate)/(total number of moles of carboxylate compound)×100

Synthesis Example 1

(Preparation of 2-ethylidene Norbornane by Hydrogenation of 5-ethylidene-2-norbornene (ENB))

A stainless steel autoclave having an internal volume of 200 mL, equipped with a magnetically induced stirrer, three inlet nozzles at an upper part, and one extraction nozzle at a bottom part, and capable of controlling the internal temperature through a jacket was charged with 2.0 g of a Cu—Cr catalyst ("N-2035" available from JGC Catalysts and Chemicals Ltd.) and 30 g of heptane (guaranteed grade, available from Wako Pure Chemical Corporation) and activated for 1 hour at 170° C. with a hydrogen pressure of 1 MPaG. After cooling, 100 g of 5-ethylidene-2-norbornene (available from Tokyo Chemical Industry Co., Ltd.) was further added, and the mixture was stirred and subjected to a hydrogenation reaction for 2 hours at 90° C. under a hydrogen pressure of 2 MPaG. The reaction solution was filtered to remove the catalyst, and heptane, which is a solvent, was distilled off, and 89 g of a liquid reaction product (hereinafter, may also be referred to as a "reaction solution") containing 2-ethylidene norbornane at a concentration of 95 mass % and 2-ethyl norbornane at a concentration of 5 mass % was obtained (yield: 88 mol % (the yield was calculated from the total number of moles of the 2-ethylidene norbornane and 2-ethyl norbornane relative to the number of moles of the raw material 5-ethylidene-2-norbornene). The yield of 2-ethylidene norbornane was 84 mol % (calculated from the number of moles of 2-ethylidene norbornane relative to the number of moles of 5-ethylidene-2-norbornene).

The reaction equation is shown below.

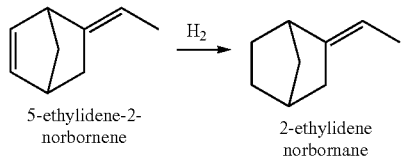

5-ethylidene-2-norbornene   2-ethylidene norbornane

Example 1

Production of ethyl 2-ethylnorbornane-2-carboxylate through Carbonylation and Esterification of 2-ethylidene norbornane An experiment was conducted using a stainless steel autoclave capable of controlling the internal temperature through a jacket. The autoclave had an internal volume of 500 mL and was equipped with a magnetically induced stirrer, three inlet nozzles at an upper part, and one extraction nozzle at a bottom part.

First, the inside of the autoclave was purged with carbon monoxide, after which 158 g (7.9 mol) of hydrogen fluoride was introduced, and the liquid temperature was adjusted to 0° C., and subsequently, the pressure was increased to 2 MPaG with carbon monoxide.

While the reaction temperature and the reaction pressure were maintained at 0° C. and 2 MPaG, respectively, a mixed solution of 82 g of the reaction solution prepared in Synthesis Example 1 (2-ethylidene norbornane concentration: 95 mass %, 2-ethyl norbornane concentration: 5 mass %) and 82 g of heptane (guaranteed grade, available from Wako Pure Chemical Corporation) was supplied from the upper part of the autoclave for 60 minutes, and a carbonylation reaction was carried out. After the supply of the raw material was ended, stirring was continued for approximately 20 minutes until absorption of carbon monoxide was no longer observed.

Subsequently, while the reaction temperature was maintained at 0° C., 46 g of ethanol (1.0 moles, molar ratio of 1.6 time with respect to the raw material 2-ethylidene norbornane) was supplied from the upper part of the autoclave for 15 minutes, and esterification was performed for 1 hour under stirring. The reaction solution was extracted from the bottom of the autoclave into ice water, and the oil phase and the aqueous phase were separated, after which the oil phase was washed twice with 100 mL of a 2 mass % sodium hydroxide aqueous solution and twice with 100 mL of distilled water, and then dehydrated with 10 g of anhydrous sodium sulfate.

Low-boiling-point substances were removed from the obtained liquid using an evaporator, after which the liquid was subjected to rectification (distillation temperature: 150° C., vacuum degree: 60 torr) with a rectifier having a theoretical plate number of 20, and then analyzed by gas chromatography using an internal standard method. As a result, the yield of the carboxylate compound (mixture of exo- and endo-isomers) was 94.1 mol % (2-ethylidene norbornane standard). The yield of the main product of ethyl 2-ethyl norbornane-2-exo-carboxylate was 84.9 mol % (2-ethylidene norbornane standard, 90.3% isomer ratio).

The main product was analyzed by GC-MS (CO, and the results indicated a molecular weight of 197.15 ([M+H]$^+$) with respect to a molecular weight of 196.29 of the targeted product. Also, the chemical shift value from $^1$H-NMR and the chemical shift value from $^{13}$C-NMR (δppm, TMS standard) in a deuterated chloroform solvent were as follows, and from these results, the main product was identified as ethyl 2-ethylnorbornane-2-carboxylate. Note that in the identification by NMR, [2] denotes a carbon atom or a hydrogen atom bonded to said carbon atom labeled by reference number 2 in the following chemical formula. The same applies below.

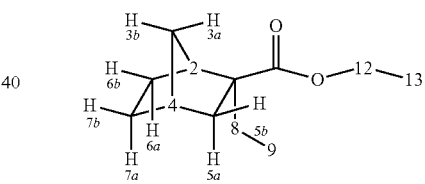

$^1$H NMR (500 MHz, CDCl$_3$) δ (ppm): 0.76 (t, J=7.5 Hz, 3H, [9]), 0.90 (dd, J=12.5, 3.0 Hz, 1H, [5a <endo>]), 1.06-1.11 (m, 1H, [7a <endo>]), 1.19-1.21 (m, 1H, [3b]), 1.23 (t, J=7.0 Hz, 3H, [13]), 1.28-1.32 (m, 1H, [3a]), 1.33-1.41 (m, 1H, [6a <endo>]), 1.45-1.50 (m, 1H, [7b <exo>]), 1.51-1.58 (m, 1H, [6b <exo>]), 1.58-1.64 (m, 2H, [8]), 2.17-2.19 (m, 1H, [4]), 2.20-2.24 (m, 1H, [5b <exo>]), 2.54 (br d, J=4.0, 1H, [2]), 4.09-4.13 (m, 2H, [12])

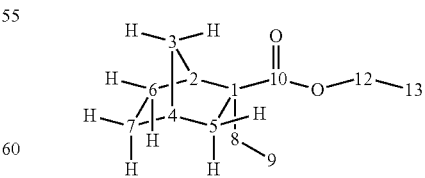

$^{13}$C NMR (126 MHz, CDCl$_3$) δ (ppm): 10.55 [9], 14.37 [13], 23.15 [6], 29.05 [7], 29.60 [8], 36.81 [4], 38.81 [3], 41.29 [5], 42.78 [2], 54.35 [1], 60.27 [12], 178.06 [10]

The ethyl 2-ethylnorbornane-2-carboxylate had a fruity-herbal-woody aroma.

Example 2

(Production of n-propyl 2-ethylnorbornane-2-carboxylate through carbonylation and esterification of 2-ethylidene norbornane)

Carbonylation, esterification, and a reaction product treatment were performed in the same manner as in Example 1 with the exception that the alcohol used in the esterification in Example 1 was replaced with n-propanol.

The obtained product was analyzed through gas chromatography, and the results indicated that the yield of the carboxylate compound was 92.9 mol % (2-ethylidene norbornane standard), and the yield of the main product n-propyl 2-ethylnorbornane-exo-2-carboxylate was 83.0 mol % (2-ethylidene norbornane standard, 89.4% isomer ratio).

The main product was analyzed by GC-MS (CO, and the results indicated a molecular weight of 211.13 ([M+H]$^+$) with respect to a molecular weight of 210.32 of the targeted product. Also, the chemical shift value from $^1$H-NMR and the chemical shift value from $^{13}$C-NMR (δppm, TMS standard) in a deuterated chloroform solvent were as follows, and from these results, the main product was identified as n-propyl 2-ethylnorbornane-2-carboxylate.

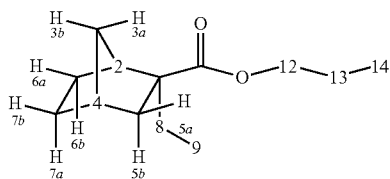

$^1$H NMR (500 MHz, CDCl$_3$) δ (ppm): 0.76 (t, J=7.5 Hz, 3H, [9]), 0.89-0.92 (m, 1H, [5b <endo>]), 0.93 (t, J=7.0 Hz, 3H, [14]), 1.05-1.11 (m, 1H, [7a <endo>]), 1.18-1.22 (m, 1H, [3b]), 1.27-1.32 (m, 1H, [3a]), 1.33-1.40 (m, 1H, [6b <endo>]), 1.45-1.51 (m, 1H, [7b <exo>]), 1.52-1.59 (m, 1H, [6a <exo>]), 1.60-1.67 (m, 4H, [13], [8]), 2.17-2.19 (m, 1H, [4]), 2.20-2.24 (m, 1H, [5a <exo>]), 2.54 (br d, J=3.5 Hz, 1H, [2]), 4.98-4.05 (m, 2H, [12])

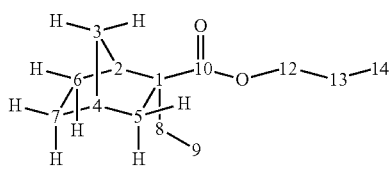

$^{13}$C NMR (126 MHz, CDCl$_3$) δ (ppm): 10.59 [9, 14], 22.16 [13], 23.16 [6], 29.06 [7], 29.64 [8], 36.82 [4], 38.82 [3], 41.30 [5], 42.80 [2], 54.52 [1], 65.98 [12], 178.14 [10]

Moreover, n-propyl 2-ethylnorbornane-2-carboxylate had a fruity-woody-herbal aroma.

Example 3

(Production of isopropyl 2-ethylnorbornane-2-carboxylate through carbonylation and esterification of 2-ethylidene norbornane)

Carbonylation, esterification, and reaction product treatment were performed in the same manner as in Example 1 with the exception that the alcohol used in the esterification in Example 1 was replaced with isopropanol.

The obtained product was analyzed through gas chromatography, and the results indicated that the yield of the carboxylate compound was 92.4 mol % (2-ethylidene norbornane standard), and the yield of the main product isopropyl 2-ethylnorbornane-2-exo-carboxylate was 81.2 mol % (2-ethylidene norbornane standard, 87.9% isomer ratio).

The main product was analyzed by GC-MS (CO, and the results indicated a molecular weight of 211.12 ([M+H]$^+$) with respect to a molecular weight of 210.32 of the targeted product. Also, the chemical shift value from $^1$H-NMR and the chemical shift value from $^{13}$C-NMR (δppm, TMS standard) in a deuterated chloroform solvent were as follows, and from these results, the main product was identified as isopropyl 2-ethylnorbornane-2-carboxylate.

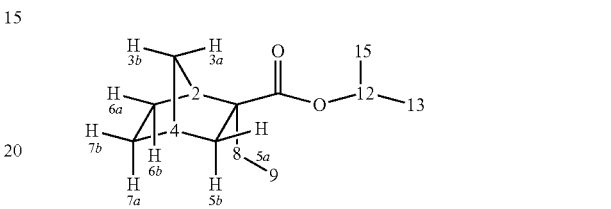

$^1$H NMR (500 MHz, CDCl$_3$) δ (ppm): 0.76 (t, J=7.0 Hz, 3H, [9]), 0.87-0.90 (m, 1H, [5b<endo>]), 1.05-1.11 (m, 1H, [7a <endo>]), 1.19-1.21 (m, 7H, [3b], [13], [15]), 1.29-1.30 (m, 1H, [3a]), 1.33-1.39 (m, 1H, [6b <endo>]), 1.45-1.51 (m, 1H, [7b <exo>]), 1.51-1.56 (m, 1H, [6a <exo>]), 1.56-1.64 (m, 2H, [8]), 2.16-2.19 (m, 1H, [4]), 2.19-2.22 (m, 1H, [5a <exo>]), 2.54 (br d, J=4.0 Hz, 1H, [2]), 4.96-5.01 (m, 1H, [12])

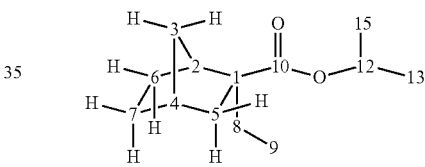

$^{13}$C NMR (126 MHz, CDCl$_3$) δ (ppm): 10.47 [9], 21.85-21.88 [13], [15], 23.16 [6], 29.08 [7], 29.53 [8], 36.80 [4], 38.74 [3], 41.25 [5], 42.79 [2], 54.25 [1], 67.22 [12], 177.49 [10]

Moreover, isopropyl 2-ethylnorbornane-2-carboxylate had an herbal-fruity-apple-woody aroma.

Example 4

Fragrance Composition

According to the formulation of Table 1 below, a floral-fruity fragrance composition was prepared using the carboxylate compound obtained in Example 1.

TABLE 1

| Formulation | parts by mass |
|---|---|
| Benzaldehyde | 3 |
| Citronellol | 70 |
| CYCLACET (trade name) | 140 |
| (Available from International Flavors & Fragrances, Inc.) | |
| γ-decalactone | 10 |
| Dimethylbenzylcarbinyl acetate | 80 |
| Ethyl phenylacetate | 6 |
| GALAXOLIDE (trade name) | 180 |
| (Available from International Flavors & Fragrances, Inc.) | |
| 50BB: 50% in benzyl benzoate | |
| Geraniol | 85 |

TABLE 1-continued

| Formulation | parts by mass |
|---|---|
| Linalool | 80 |
| γ-Methylionone | 30 |
| Phenylethyl alcohol | 155 |
| Rose oxide | 6 |
| TRIPLLAL (trade name) (Available from International Flavors & Fragrances, Inc.) | 5 |
| VERTENEX (trade name) (Available from International Flavors & Fragrances, Inc.) | 100 |
| Compound of Example 1 | 50 |
| Total | 1000 |

A sensory evaluation was conducted by four panelists with five or more years of experience, and the results indicated that all of the panelists found that the floral-fruity fragrance composition containing the compound of Example 1 had a strong fruity aroma, excellent palatability, and superior diffusivity.

INDUSTRIAL APPLICABILITY

The novel carboxylate compound of the present invention has a fruity aroma, and the aroma thereof is excellent, and therefore the carboxylate compound of the present invention is effective as a perfuming component in a wide range of applications such as in toiletry articles, soaps, and clothing detergents. Furthermore, according to the method for producing a carboxylate compound of the present invention, the carboxylate compound can be produced in an industrially advantageous manner.

The invention claimed is:

1. A carboxylate compound represented by Formula (1):

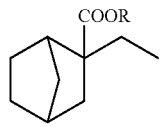

(1)

where, R is an alkyl group having from 2 to 6 carbons.

2. The carboxylate compound according to claim 1, wherein R is an ethyl group, a n-propyl group, or an isopropyl group.

3. A fragrance composition comprising a carboxylate compound represented by Formula (1):

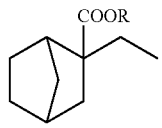

(1)

where, R is an alkyl group having from 2 to 6 carbons.

4. A method for producing a carboxylate compound represented by Formula (1) by reacting a compound represented by Formula (2) with carbon monoxide in the presence of hydrogen fluoride, and then reacting with an alcohol having from 2 to 6 carbons:

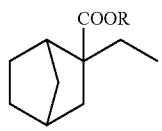

(1)

where, R is an alkyl group having from 2 to 6 carbons

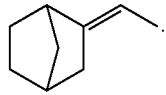

(2)

* * * * *